United States Patent
Knoth et al.

(10) Patent No.: US 10,478,111 B2
(45) Date of Patent: Nov. 19, 2019

(54) SYSTEMS FOR SPEECH-BASED ASSESSMENT OF A PATIENT'S STATE-OF-MIND

(71) Applicant: SRI International, Menlo Park, CA (US)

(72) Inventors: Bruce Knoth, San Carlos, CA (US); Dimitra Vergyri, Sunnyvale, CA (US); Elizabeth Shriberg, Berkeley, CA (US); Vikramjit Mitra, Fremont, CA (US); Mitchell McLaren, Sunnyvale, CA (US); Andreas Kathol, El Cerrito, CA (US); Colleen Richey, Foster City, CA (US); Martin Graciarena, Belmont, CA (US)

(73) Assignee: SRI International, Menlo Park, CA (US)

( * ) Notice: Subject to any disclaimer, the term of this patent is extended or adjusted under 35 U.S.C. 154(b) by 12 days.

(21) Appl. No.: 15/505,577

(22) PCT Filed: Aug. 5, 2015

(86) PCT No.: PCT/US2015/043862
§ 371 (c)(1),
(2) Date: Feb. 21, 2017

(87) PCT Pub. No.: WO2016/028495
PCT Pub. Date: Feb. 25, 2016

(65) Prior Publication Data
US 2018/0214061 A1    Aug. 2, 2018

Related U.S. Application Data

(60) Provisional application No. 62/040,965, filed on Aug. 22, 2014.

(51) Int. Cl.
*G10L 15/10* (2006.01)
*A61B 5/16* (2006.01)
(Continued)

(52) U.S. Cl.
CPC .......... *A61B 5/165* (2013.01); *G06N 20/00* (2019.01); *G10L 15/1807* (2013.01);
(Continued)

(58) Field of Classification Search
CPC combination set(s) only.
See application file for complete search history.

(56) References Cited

U.S. PATENT DOCUMENTS 6,424,946 B1   7/2002  Tritschler
9,058,816 B2 * 6/2015  Lech ................ G10L 17/26
(Continued)

FOREIGN PATENT DOCUMENTS

| JP | 2000-245718 | 9/2000 |
| JP | 2004-233691 | 8/2004 |
| JP | 2004-240394 | 8/2004 |

OTHER PUBLICATIONS

Mitra et al.; Articulatory trajectories for large-vocabulary speech recognition; 2013 IEEE International Conference on Acoustics, Speech & Signal Processing; 2013, pp. 7145-7149, 5p (Year: 2013).*

(Continued)

*Primary Examiner* — Abul K Azad
(74) *Attorney, Agent, or Firm* — Hickman Palermo Becker Bingham LLP; Christine E. Orich (57) ABSTRACT

A computer-implemented method can include a speech collection module collecting a speech pattern from a patient, a speech feature computation module computing at least one speech feature from the collected speech pattern, a mental health determination module determining a state-of-mind of (Continued)

the patient based at least in part on the at least one computed speech feature, and an output module providing an indication of a diagnosis with regard to a possibility that the patient is suffering from a certain condition such as depression or Post-Traumatic Stress Disorder (PTSD).

27 Claims, 9 Drawing Sheets

(51) Int. Cl.
  *G06N 20/00* (2019.01)
  *G10L 17/26* (2013.01)
  *G10L 15/18* (2013.01)
  *G10L 25/63* (2013.01)
  *G10L 25/66* (2013.01)

(52) U.S. Cl.
  CPC .......... *G10L 15/1822* (2013.01); *G10L 17/26* (2013.01); *G10L 25/63* (2013.01); *G10L 25/66* (2013.01)

(56) References Cited

U.S. PATENT DOCUMENTS

| | | | |
|---|---|---|---|
| 9,160,852 B2 | 10/2015 | Ripa | |
| 9,208,778 B2 | 12/2015 | Chopra | |
| 9,800,721 B2* | 10/2017 | Gainsboro | H04M 3/2281 |
| 9,818,410 B2 | 11/2017 | Sak | |
| 9,965,553 B2* | 5/2018 | Lyren | G06F 17/30864 |
| 2003/0078768 A1 | 4/2003 | Silverman et al. | |
| 2004/0158465 A1 | 8/2004 | Rees | |
| 2005/0102135 A1 | 5/2005 | Goronzy | |
| 2008/0256576 A1 | 10/2008 | Nesvabda | |
| 2009/0043586 A1* | 2/2009 | MacAuslan | G10L 17/26 704/270 |
| 2009/0063605 A1 | 3/2009 | Nakajima | |
| 2012/0116186 A1 | 5/2012 | Shrivastav et al. | |
| 2013/0166291 A1* | 6/2013 | Lech | G10L 17/26 704/232 |
| 2014/0095150 A1 | 4/2014 | Berjikly | |
| 2014/0163960 A1 | 6/2014 | Dimitriadis | |
| 2014/0249823 A1* | 9/2014 | Hayakawa | G10L 17/26 704/270 |
| 2015/0213800 A1 | 7/2015 | Krishnan | |
| 2015/0318002 A1* | 11/2015 | Karam | A61B 5/7264 704/231 |
| 2016/0071520 A1* | 3/2016 | Hayakawa | G10L 17/04 704/247 |
| 2016/0111086 A1 | 4/2016 | Ziolko | |

OTHER PUBLICATIONS

Liu etal.; Cough signal recognition with Gammatone Cepstral Coefficients; 2013 IEEE China Summit and International Conference on Signal and Information Processing Signal and Information Processing (ChinaSIP), 2013 IEEE China Summit & International Conference on; Jul. 2013; pp. 160-164. (Year: 2013).*
France et al.: "Acoustical Properties of Speech as Indicators of Depression and Suicidal Risk", IEEE Transactions on Biomedical Engineering, IEEE Service Center, vol. 47, No. 7, Jul. 1, 2000, 9 pages.
Extended Search Report and Written Opinion for European Application No. 15834564.5, dated Aug. 11, 2017, 8 pages.
Written Opinion of the International Searching Authority for PCT/US2015/043862 dated Nov. 4, 2015, 5 pages.
Tsiartas, U.S. Appl. No. 15/179,816, filed Jun. 10, 2016, Office Action, dated Mar. 12, 2019.
Low et al., "Detection of Clinical Depression in Adolescents Speech During Family Interactions", IEEE Transactions on Biomedical Engineering, vol. 58, No. 3, dated Mar. 2011, 13 pages.
Helfer et al, "Classification of Depression State Based on Articulatory Precision", In Interspeech dated 2013, 5 pages.
European Patent Office, "Search Report" in application No. 15 834 564.5-1207, dated May 15, 2019, 7 pages.
European Claims in application No. 15 834 564.5-1207, dated May 2019, 2 pages.
Cen et al., "Speech Emotion Recogniton Using Canonical Correlation Analysis and Probabilistic Neural Network", 2008 Seventh International Conference on Machine Learning and Applications, 4 pages.
Notice of Grounds for Rejection in application No. 2017-509749, dated Jun. 26, 2019, 6 pages.
Current Claims in application No. PCT/US2015/043862, dated Jun. 2019, 3 pages.

* cited by examiner

SYSTEMS FOR SPEECH-BASED ASSESSMENT OF A PATIENT'S STATE-OF-MIND

CROSS-REFERENCE TO RELATED APPLICATION

This application is a § 371 U.S. National Stage of International Application Serial No. PCT/US2015/043862, titled SYSTEMS FOR SPEECH-BASED ASSESSMENT OF A PATIENT'S STATE-OF-MIND and filed on Aug. 5, 2015, which claims the benefit of U.S. Provisional Patent Application Ser. No. 62/040,965, titled METHOD AND APPARATUS FOR DETECTION AND MEASUREMENT OF PTSD AND DEPRESSION and filed on Aug. 22, 2014, the contents of which are hereby fully incorporated by reference herein.

STATEMENT REGARDING FEDERALLY SPONSORED RESEARCH AND DEVELOPMENT

This invention was made with Government support under United States Army Medical Research Acquisition Activity contract no. W81XWH-11-C-0004 and also National Science Foundation grant no. U.S. Pat. No. 1,162,046. The Government has certain rights in this invention.

BACKGROUND

Speech offers important benefits for mental health monitoring, especially since certain conditions such as depression are common mental health problems that have significant impact on human society but often go undetected. Speech analysis is noninvasive, natural, inexpensive, and can be used in a number of emerging areas such as telemedicine applications for remote assessments, for example.

There is evidence in the psycholinguistics literature that speech contains important information that may assist psychiatrists during clinical assessment. Central controls of laryngeal, pharyngeal, and nasal structures tend to generate several objectively measurable expressions of emotional stress. Mental health problems including schizophrenia, depression, and psychopathy, for example, generally affect prosody. Indeed, psychological health appears to be intimately linked to producing certain types of speech characteristics.

An important challenge is individual differences, which are typically large and can obscure inter-speaker effects associated with mental health. As part of a larger effort on longitudinal speaker-state modeling, speech characteristics that correlate with clinical assessments about a patients suicide risk may be identified.

A new corpus of real patient-clinician interactions recorded when patients are admitted to a hospital for suicide risk may be analyzed, and again when the patients are released. For privacy reasons, only non-lexical features are typically used. Specific changes to automatically extracted speech features that correlate with a clinician's assessment for a patient's depression state may be identified.

Indeed, various prior studies have attempted to identify speech characteristics that can detect different psychological conditions.

DETAILED DESCRIPTION

Advances in the fields of speech technology and machine learning have made it possible to use complex patterns in people's (e.g., patients') speech to predict the speakers' mental states (e.g., as defined by various clinical protocols). Such systems and processes directed to using speech to predict mental state generally begin with the collecting of speech data from a speaker (e.g., a patient). The system or process may then derive mathematical parameters (also referred to herein as speech features) from the collected speech data. The system or process may then compare those values with data in a pre-defined set of features and associated mental states, e.g., in order to determine the likely status of the speaker. This result may then be presented to the speaker and/or clinicians, e.g., as appropriate.

Collecting a patient's speech data has historically been done by the recording of clinician-guided interviews with the subject using a tape recorder or, more recently, a digital audio recorder. Such processes of recording interviews, however are cumbersome. For example, specialized equipment is required, such equipment must be configured properly, the interviewer and interviewee typically wear microphones, and an interviewer must conduct the interview.

In contrast, certain implementations of the disclosed technology may include an application-based, automated speech-elicitation program. Such programs may focus solely on the collecting of speech data. Alternative implementations may also automate analysis of the collected speech and/or presentation of data.

In certain embodiments, a patient's speech data may be collected by way of the audio hardware of a mobile electronic device such as a smartphone or tablet, for example. An application installed on the device may cause the device to ask the user open-ended questions, e.g., pertaining to recent events. The device may also record the user's responses to the questions. The questions presented to the patient may be designed so that they can be answered frequently (e.g., weekly) and/or with extended answers (e.g., neither "yes questions" nor "no questions"). It should be noted that such questions may intentionally avoid probing the speaker's mental state directly or delving deeply into the speaker's feelings.

The order of the questions may be randomized for each patient and/or each session, e.g., so that the speaker will be asked different questions every time he or she uses the application. It should be noted that, because the sequence is random, the subject may at times hear questions repeated from prior sessions.

In certain implementations, a certain amount of speech may be recorded during each session (e.g., a total of two minutes of recordings for a given session). Once the patient has responded to questions for such specified total amount of time, the application may thank the subject for participating and terminate the session. The application may also upload the recordings to a server, e.g., locally or remote.

Certain implementations generally pertain to systems and methods for analyzing the speech features of a patient in order to perform a mental health assessment of the patient, e.g., in order to determine a score corresponding to post traumatic stress disorder (PTSD) or depression the patient may be suffering from, for example. Indeed, a patient's speech features contain important information that can be used to help detect the PTSD or depression status of a patient, for example.

In certain embodiments, speech features may be used to assess the PTSD or depression status of a patient as an individual's speech features, e.g., drawn from a recorded Counseling and Psychological Services (CAPS) interview, generally correlate to the diagnosis of PTSD or depression for a person. Recorded interviews from a patient population may be used to develop and test an objective scoring system for ultimately providing an assessment score indicating or otherwise related to a PTSD or depression status of a patient.

Certain implementations of the disclosed technology may include the use of a protocol to select, prepare, and analyze recorded interviews from a patient population screened for PTSD or depression. The population may include both PTSD-negative and PTSD-positive patients, for example, and the protocol may include appropriate informed-consent procedures and procedures for de-identifying the data, e.g., to eliminate the 18 Health Insurance Portability and Accountability Act (HIPAA) identifiers (45 C.F.R. § 164.514 (b)(2)(i)(A)-(R)). The interviews may be transcribed, and the recordings may be segmented into separate interviewer and interviewee units.

In certain embodiments, prosodic features may be defined and extracted from an individual interviewee's recording segments. These features may include any of a number of various parameters such as phonetic and pause durations as well as measurements of pitch and energy over various extraction regions. Any of a number of established automated speech recognition techniques may be used to transcribe these segments.

In certain embodiments, Mel frequency cepstral coefficients (MFCCs) and pitch and energy features may be extracted from the patient interviews. Other features may include novel cepstral features and temporal variation parameters (such as speaking rate, distribution of prominence peaks in time, pause lengths and frequency, and syllable durations, for example), speech rhythmicity, pitch variation, and voiced/voiceless ratios. Certain implementations of the disclosed technology may be restricted to automatically extractable features that do not rely on words, e.g., for reasons of patient privacy and also practicality. For each manually annotated segment in a patient channel, a range of speech feature types intended to capture potential PTSD or depression markers may be computed. Such features may be divided into two categories: low-level features computed from short speech samples (e.g., 20 ms in length) and high-level temporal features, computed from long speech samples (e.g., at the utterance level).

The low-level features may include any one or combination of the following: Damped Oscillator Cepstral Coefficients (DOCC), Normalized Modulation Cepstral Coefficients (NMCCs), Medium Duration Speech Amplitudes (MMeDuSA) features, Gammatone Cepstral Coefficients (GCCs), DeepTVs, and Acoustic Phonetic (AP) features.

Damped Oscillator Cepstral Coefficients (DOCC) may aim to model the dynamics of the hair cells within the human ear. These hair cells generally detect the motion of incoming sound waves and excite the neurons of the auditory nerves. In DOCC processing, the incoming speech signal may be analyzed by a bank of gammatone filters (e.g., a bank of 40 gammatone filters equally spaced on the equivalent rectangular bandwidth (ERB) scale), which generally splits the signal into bandlimited subband signals. In turn, these subband signals may be used as the forcing functions to an array of damped oscillators whose response may be used as the acoustic feature.

Normalized Modulation Cepstral Coefficients (NMCCs) may track the amplitude modulation (AM) trajectories of time-domain sub-band speech signals, e.g., using a Hamming window along with the Discrete Energy Separation algorithm (DESA), which generally play an important role in human speech perception and recognition.

Modulation of Medium Duration Speech Amplitudes (MMeDuSA) features may be used to track the sub-band AM signals and the overall summary modulation of speech, e.g., using a medium-duration analysis window. Summary modulation may play an important role in tracking speech activity and in locating events such as vowel prominence/stress.

Gammatone Cepstral Coefficients (GCCs) may use a perceptually motivated gammatone filterbank to analyze a speech signal. An algorithm for GCCs may compute a gammatone spectrum and extract cepstral features after performing a discrete cosine transform on root-compressed filterbank energies. In GCC processing, speech may be analyzed using a bank of 40 gammatone filters equally spaced on the ERB scale, for example.

DeepTVs are a set of articulatory features that may be obtained from a deep neural network that estimates constriction locations and degrees at various parts of the vocal tract. These features are eight-dimensional and generally capture information such as glottal and velic opening/closing, labial constriction, lip rounding, and tongue tip and tongue blade constrictions.

Acoustic Phonetic (AP) features generally represent acoustic-phonetic information (e.g., formant information, mean Hilbert envelope, periodic and aperiodic energy in subbands, etc.) and may be analyzed at a 5-msec frame rate with a 10-msec analysis window.

A Kaldi Pitch tracker may be used to provide a two-dimensional output: pitch tracks and a normalized cross-correlation function that gives indication about voicing information, for example.

The high-level features may include any one or combination of the following: tilt features, Dev features, energy contour (En-con) features, pitch-related features, and intensity-related features.

Tilt features generally aim to capture vocal effort given extrinsic session variability. Features may be extracted for voiced frames. For example, five-component tilt features may include three that reflect lower-order harmonics and formants given the microphone and room conditions: H2-H1, F1-H1, and F2-H1. The last two features may include measures that are the spectral slope per frame, and the difference between the maximum of the log power spectrum and the maximum in the 2 kHz-3 kHz range, for example.

DLE features may target session-normalized vocal effort detection using a sparse feature (e.g., output only once per voiced-voiceless transition). The feature is generally the difference in log energy at the transition. DLE-onset features are typically triggered at each boundary from voiceless to voiced speech, whereas dev-offset features usually occur at each boundary from voiced to voiceless speech.

An energy contour (En-con) feature set generally aims to capture rhythmicity by looking at the periodicity of energy peaks within each segment. This feature typically models the contour of 10-ms c0 and c1 output from an MFCC front end, where each cepstral stream may be mean-normalized over the utterance, thus making it robust to absolute level differences over both sessions and within-session segments. A discrete cosine transform may then be taken over a 200-ms sliding window with a 100-ms shift. For each window, vector components may include the first five DCT bases for c0 and the first two bases for c1.

Pitch-related features generally include f0, f0pk, and f0pk-stats features. The f0-peak features generally record only the subset of pitch values found by an automatic peak-picking algorithm that is run within each segment. Statistics computed in the f0peak-stats features may include both pitch-level and pitch-peak distribution information. Pitch-level generally includes the mean, max, and standard deviation of the peak pitches in the segment. Pitch-peak distributions are typically intended to capture not pitch, but rather the temporal distribution of pitch-accented syllables in the segment. These features may include any of the following: peak count, peak rate (e.g., count divided by segment duration), mean and maximum interpeak distances, and location of the maximum peak in the segment (e.g., early vs. late), both as a percentage of the duration of the segment and as a raw distance into the segment.

Intensity-related features such as int, intpk, and intpk-stats may be computed in a manner similar to those for the pitch features, but for intensity rather than pitch. Unlike pitch, raw intensity values (e.g., intensity, intensity at peaks, and mean/max/stdev of intensity) may reflect not only the speaker but also the recording session. Remaining intpk-stats features, such as those for f0-peak stats, may aim to capture the distribution of pitch accents in a segment and may be interpreted as only behavioral features.

In certain embodiments, lexical features may be extracted from an interviewee's transcripts. These features may include disfluencies, idea density, referential activity, analysis of sentiment, topic modeling, and semantic coherence, for example.

In certain embodiments, feature selection may be performed via univariate analysis and machine-learning algorithms may be applied to develop models that predict outcome measures, such as PTSD or depression status, and aspects of the CAPS scores on the basis of acoustic and lexical feature inputs. Statistical models may be trained to identify PTSD-positive patients and PTSD-negative patients using newly extracted features, for example.

PTSD or depression assessment models may be validated using generated acoustic and lexical features. For example, three classifiers (e.g., Gaussian backend (GB), decision trees (DT) and neural networks (NN)) may be used. In certain implementations using the GB classifier, a certain number of features (e.g., the best four features) may be selected and a system combination (e.g., fusion) may be run on the subjects' speech. Certain embodiments may include the creation of PTSD classifiers that use acoustic and prosodic speech features that do not rely on lexical information. Such embodiments may also include identifying a subset that produces classification results that are significantly better than chance. Fusion of these classifiers generally results even better results. Such fusion typically provides more accurate estimations than typical clinician evaluations, for example.

A speaker (e.g., a patient speaking to or otherwise speaking in connection with an assessment system) may have a mental health condition affecting his or her speech in multiple ways. For example, a speech production apparatus (e.g., a patient's mouth) may provide short-term spectral features such as Cepstrum, whereas language and prosody patterns (e.g., from the patient's brain) may provide phrase-level prosodic/stylistic features and lexical/content features. All of these features may be provided to an algorithmic assessment in accordance with the techniques described herein.

Figure 1:
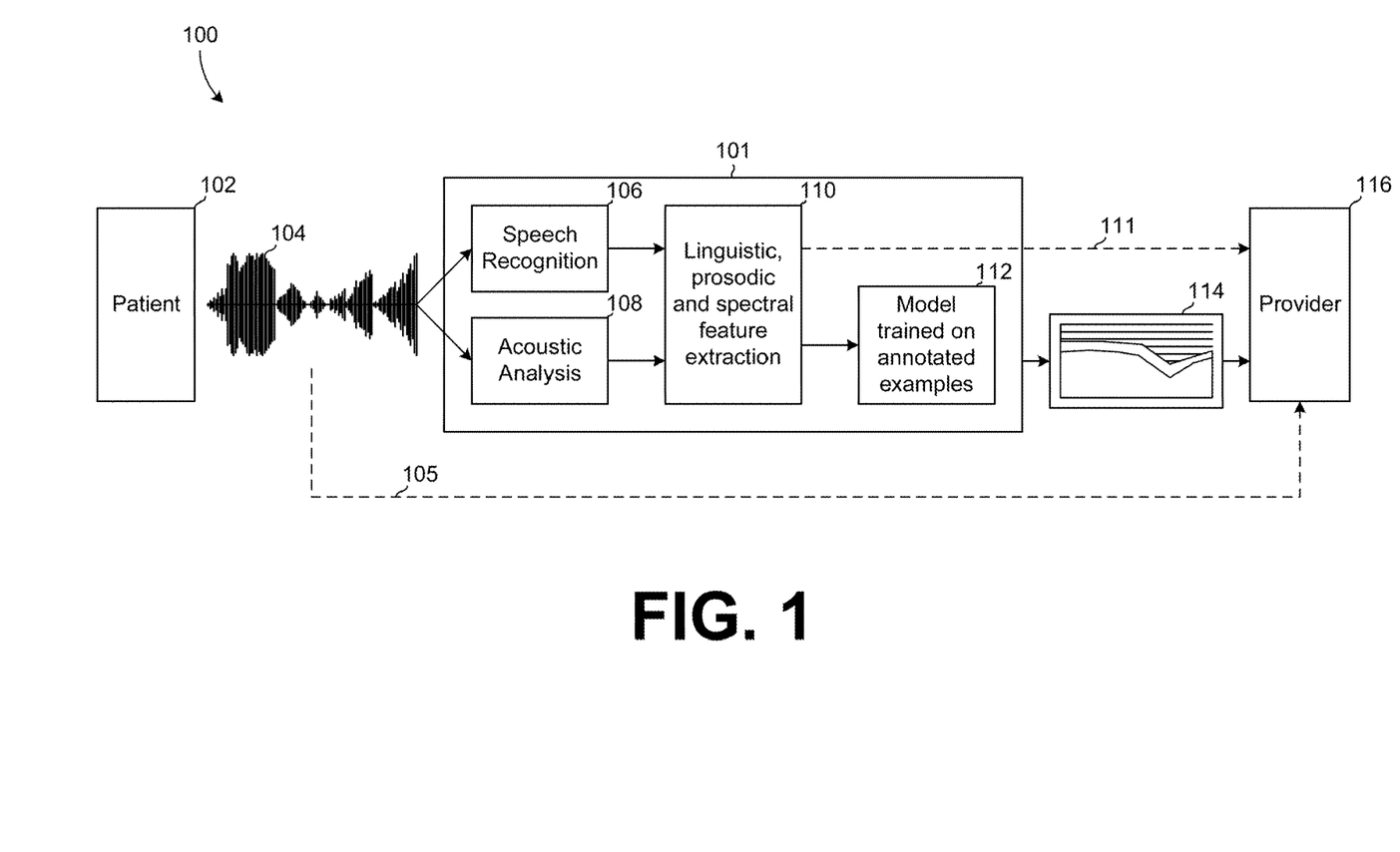
FIG. 1 is a block diagram illustrating an example of a speech-based mental health assessment system in accordance with certain embodiments of the disclosed technology.

FIG. 1 is a block diagram illustrating a first example of a speech-based mental health assessment system 100 in accordance with certain embodiments of the disclosed technology. The system 100 may be used to identify voice biomarkers that can serve as indicators for a particular mental health condition such as depression, suicidal tendencies, Post-Traumatic Stress Disorder (PTSD), a concussion, bipolar disorder, anxiety disorder, mild Traumatic Brain Injury (mTBI), and schizophrenia, for example. The system 100 is advantageously non-invasive to the patient and may provide objective measures to indicate the patient's mental health status. The system 100 may also provide low-cost, effective longitudinal monitoring of the patient.

In the example, the system 100 involves a patient 102 providing a patient's speech pattern 104, e.g., by way of the patient talking, to a speech recognition module 106 and an acoustic analysis module 108 of an assessment application 101 that may be installed on a mobile electronic device such as a smartphone, for example. Each of the speech recognition module 106 and acoustic analysis module 108 is configured to provide output information to a linguistic, prosodic, and spectral feature extraction module 110.

The extraction module 110 is configured to provide a mental health assessment score 114 to a provider 116 such as a medical clinician or other suitable user. In certain embodiments, the extraction module 110 may also provide information directly to the provider 116, as indicated by 111. Alternatively or in addition thereto, the speech pattern 104 may be provided directly to the provider 116 or other suitable user of the system 100, as indicated by 105, e.g., for use in analyzing the patient in conjunction with the mental health assessment score 114.

Figure 2:
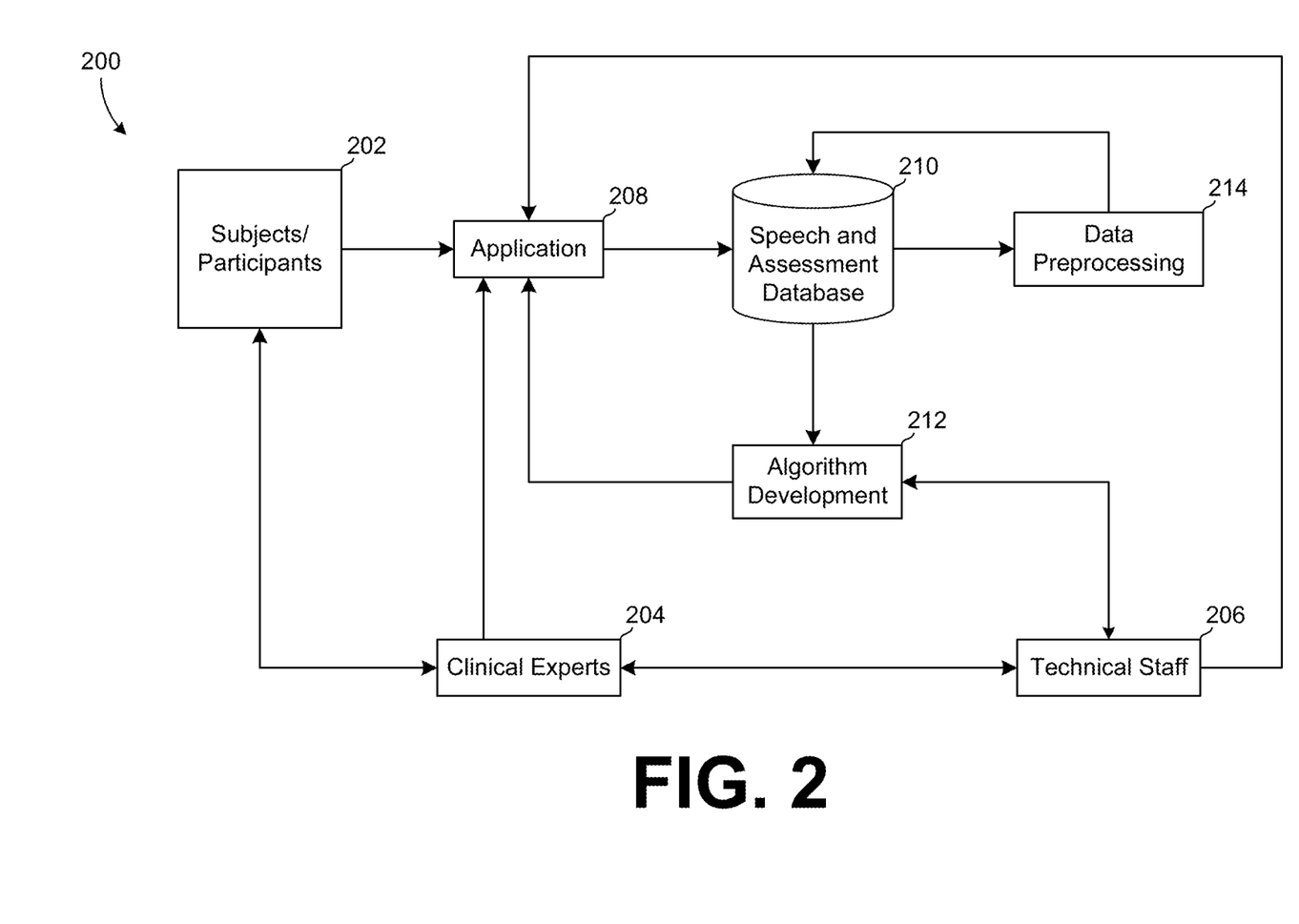
FIG. 2 is a block diagram illustrating an example of a clinical research data collection and analysis system in accordance with certain embodiments of the disclosed technology.

FIG. 2 is a block diagram illustrating an example of a clinical research data collection and analysis system 200 in accordance with certain embodiments of the disclosed technology. In the example, each of a plurality of subjects 202, e.g., patients or volunteers, may provide information to an application 208, e.g., an assessment application installable on and useable with any of a number of suitable devices such as mobile electronic devices (e.g., smartphones). This information may include speech samples, and may include self-assessment instruments through which the participants can provide information with regard to their mental state. Alternatively or in addition thereto, the subjects 202 may provide information directly to one or more clinical experts 204. One or more of the clinical experts 204 may each interact with, e.g., exchange information with, at least one of one or more technical staff 206, who may also interact with the application 208. The clinical experts may also provide data "annotations" which may include expert assessments on the status of the participants.

The application 208 may access or otherwise interact with a speech and assessment database 210, which may also interact with a data preprocessing module 214. The data preprocessing module may assess the quality of the audio, e.g., to ensure that it includes in the analysis only good speech samples, and may filter out from processing regions that are not proper for analysis such as non-speech sounds, silence, or other background events, for example. The technical staff 206 may modify as needed for the task the machine learning module 212, which may provide information to or otherwise interact with the application 208. The machine learning module 212 generally consists of a set of algorithms configured to enable the system 200 to learn models that provide scores or assessments about the speaker's mental health state based on the input speech. This learning phase may be done offline, e.g., after data and annotations from several speakers are made available through the application. Alternatively, the learning phase may be done continuously, e.g., as participants provide their self-assessments or clinical annotations after each time they use the application. Also, these models may be speaker-specific, e.g., if multiple data points are available per speaker, or speaker-independent, e.g., if there are data points from multiple speakers but only few per speaker.

Figure 3:
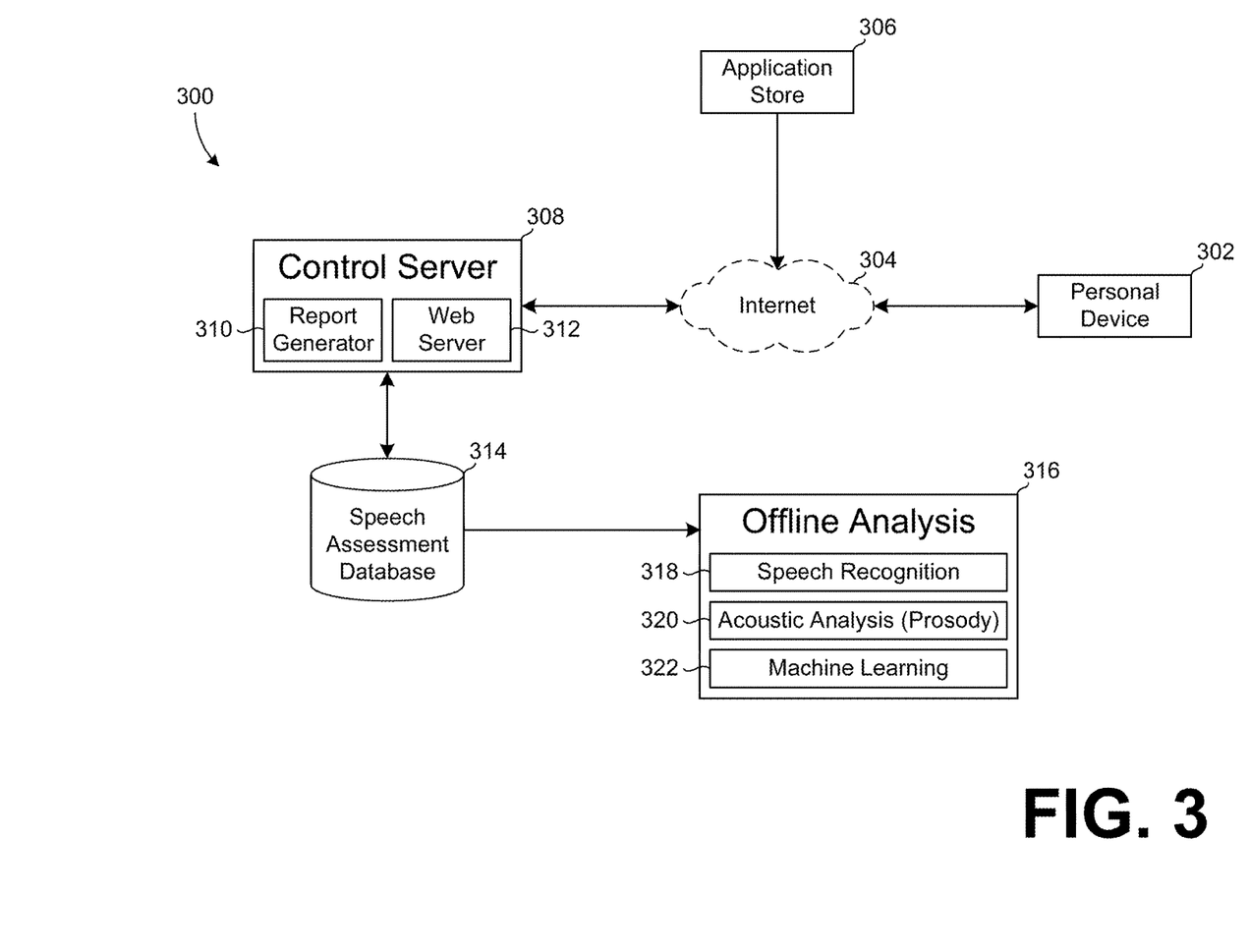
FIG. 3 is a block diagram illustrating an example of a speech-based mental health assessment and collection system in accordance with certain embodiments of the disclosed technology.

FIG. 3 is a block diagram illustrating an example of a speech-based mental health assessment and collection system 300 in accordance with certain embodiments of the disclosed technology. In the example, a personal device 302 such as a mobile electronic device (e.g., a smartphone) may download or otherwise access an application, e.g., a mobile application in accordance with the disclosed technology, at an application store 306 via the Internet 304 or other suitable network, for example. The user may download the application and register the application by providing certain personal and identifying information such as age and gender, for example.

A control server 308 may interact with either or both of the personal device 302 and the application store 306 via the Internet 304 or other suitable network. In the example, the control server 308 includes a report generator 310 and a web server 312. The report generator 310 may be configured to produce a report in any of a number of suitable formats such as a score or a graph, for example.

The control server 308 may also be configured to interact with a speech assessment database 314. In certain embodiments, the system 300 may also include an offline analysis module 316 having a speech recognition sub-module 318, an acoustic analysis sub-module 320, a machine learning module 322, or any combination thereof.

Figure 4:
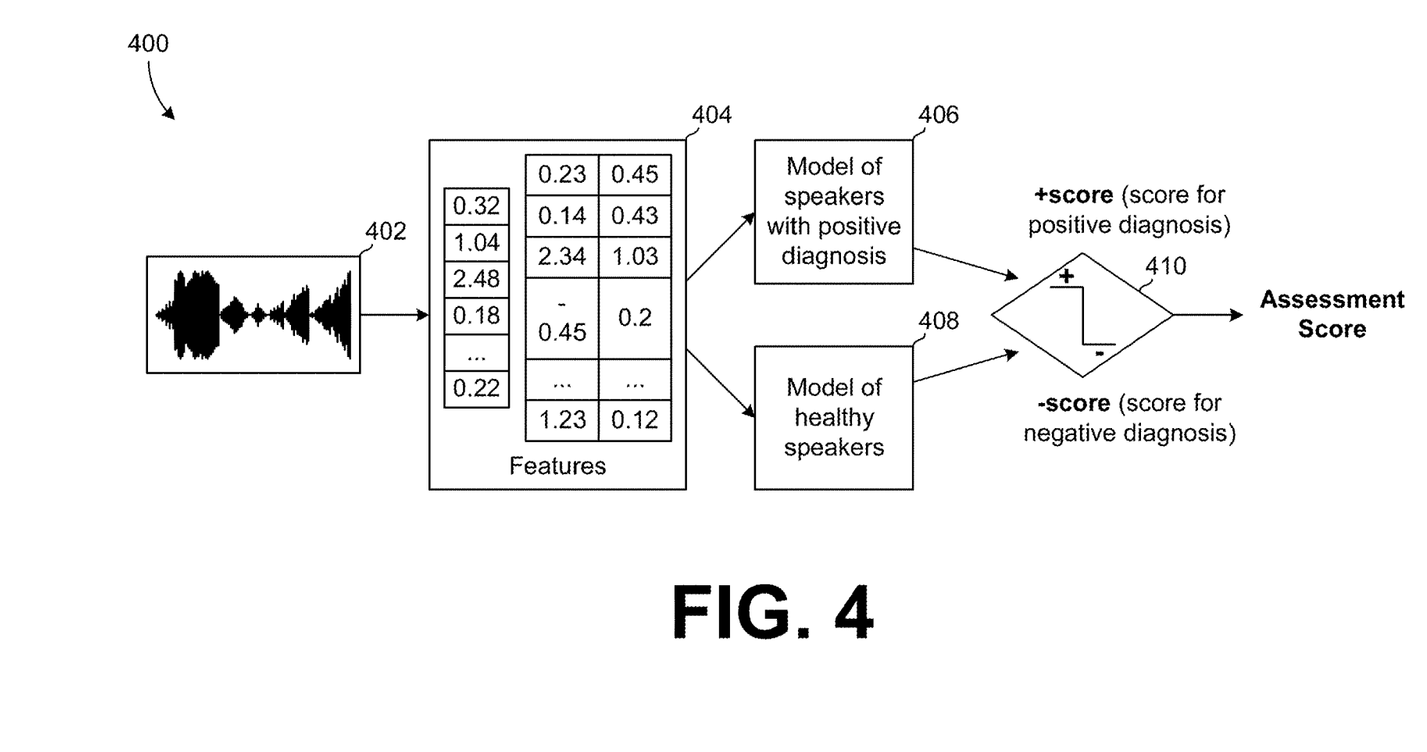
FIG. 4 is a block diagram illustrating an example of a machine learning system in accordance with certain embodiments of the disclosed technology.

FIG. 4 is a block diagram illustrating an example of a machine learning system 400 in accordance with certain embodiments of the disclosed technology. The system 400 may use clinical data to build statistical models that discriminate between positive and negative diagnoses, for example.

In the example, a speech pattern 402, e.g., from a patient talking, may be provided to a speech feature extraction module 404 (also referred to herein as a speech feature computation module). The speech feature extraction module 404 may provide output information including a first statistical model 406 of speakers having a positive diagnosis, a second statistical model 408 of healthy speakers, or both for use by a decision making module 410 in determining an assessment score, which may be a positive score, e.g., for a positive diagnosis, or a negative score, e.g., for a negative diagnosis.

The speech feature extraction module 404 may be configured to identify biomarkers, e.g., speech features that can be used to identify a condition of the speaker. The features identified by the speech feature extraction module 404 may be used to derive the target class models 406 and 408 for positive and negative diagnoses, respectively. The decision making module 410 may be configured to calibrate and compare the assessment score against an empirical threshold, for example.

Figure 5:
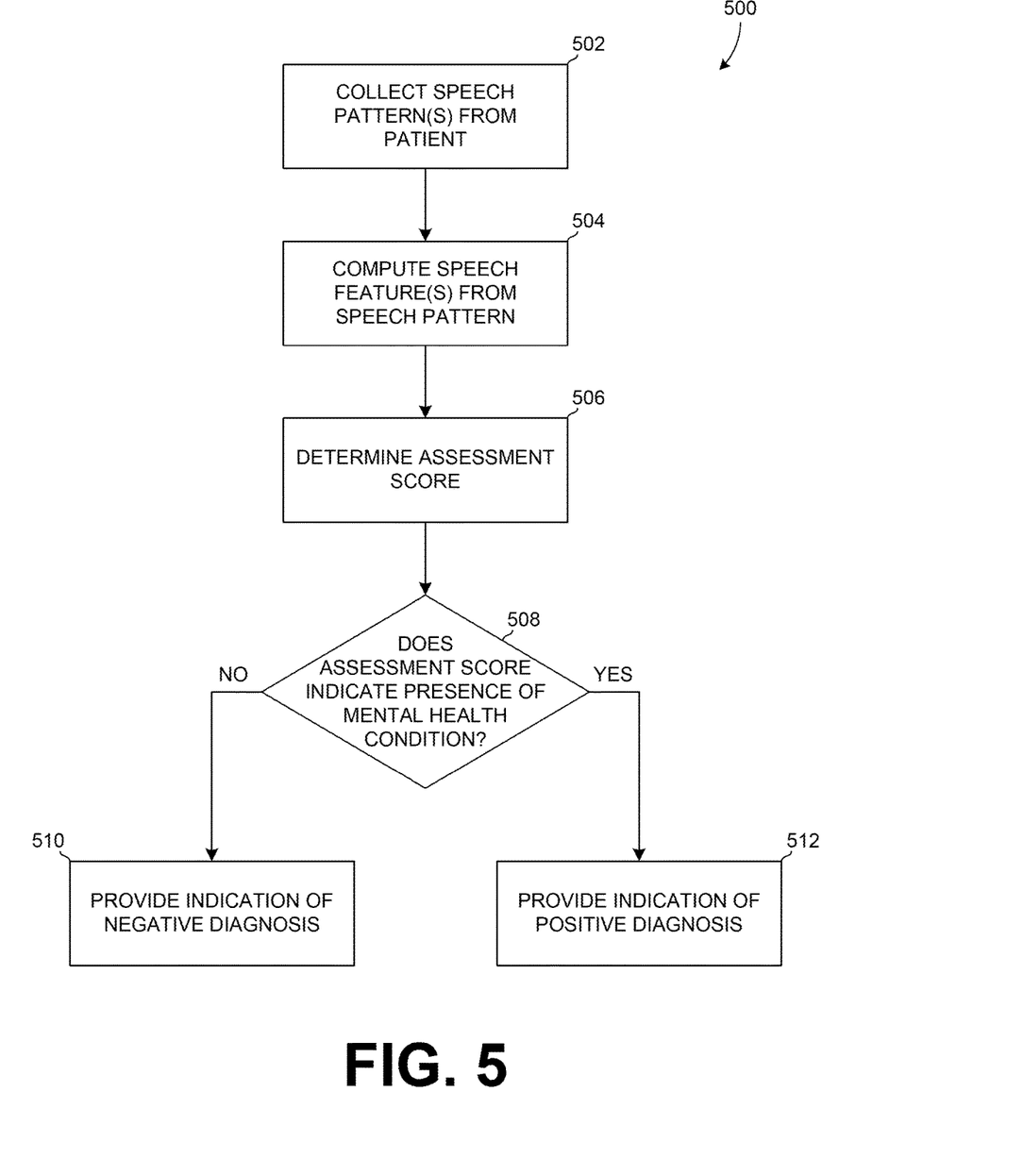
FIG. 5 is a flowchart illustrating an example of a computer-implemented method of speech-based mental health assessment in accordance with certain embodiments of the disclosed technology.

FIG. 5 is a flowchart illustrating an example of a computer-implemented method 500 of speech-based mental health assessment in accordance with certain embodiments of the disclosed technology. At 502, at least one speech pattern (such as the speech pattern 402 of FIG. 4) is collected from a patient. At 504, one or more speech features is extracted (e.g., by the speech feature extraction module 404 of FIG. 4) from the speech pattern that was collected at 502.

At 506, an assessment of the patient's state-of-mind is determined based at least in part on the speech features that were extracted at 504. At 508, a determination is made as to whether the state-of-mind assessment indicates a positive or negative diagnosis with regard to the presence of a particular mental health condition (e.g., depression, suicidal tendencies, PTSD, a concussion, bipolar disorder, anxiety disorder, mTBI, or schizophrenia). In certain implementations, the system can provide the actual assessment score, e.g., to a clinician or other medical professional.

Responsive to a determination at 508 that the state-of-mind assessment indicates a negative diagnosis (e.g., that no such mental health condition appears to be present in the patient), the system may provide an indication of the negative diagnosis as indicated at 510. Responsive to a determination at 508 that the mental health condition assessment score indicates a positive diagnosis (e.g., that there is at least a certain probability that such mental health condition is indeed present in the patient), the system may provide an indication of the positive diagnosis as indicated at 512. In certain implementations, either or both of the indications communicated at 510 and 512 may include visual alerts, audible alerts, or a particular combination thereof.

Figure 6A:
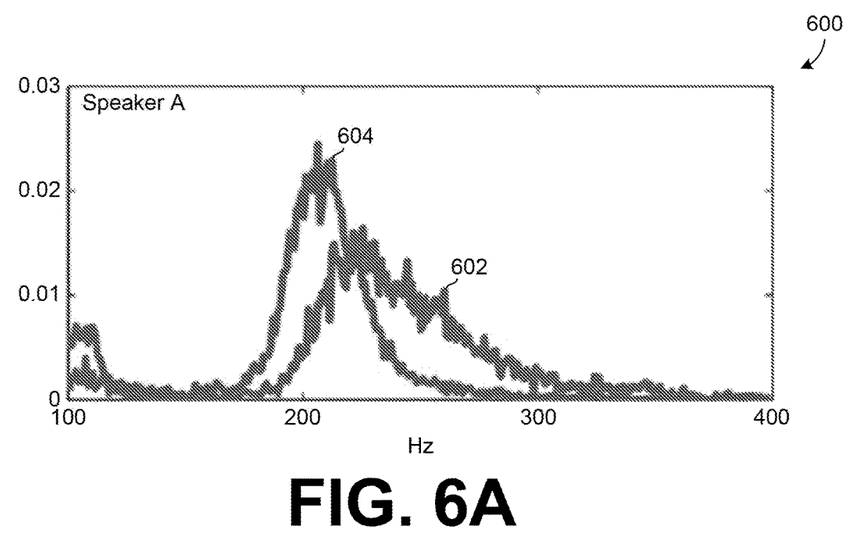
FIGS. 6A and 6B illustrate an example demonstrating how pitch distributions for two speakers may shift as they change from a stressed state to a more relaxed state.
Figure 6B:
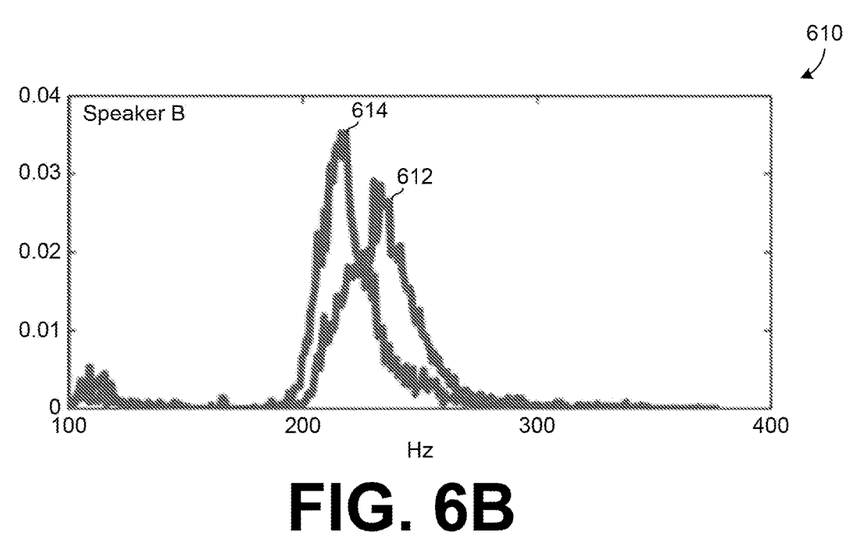
Figure 7A:
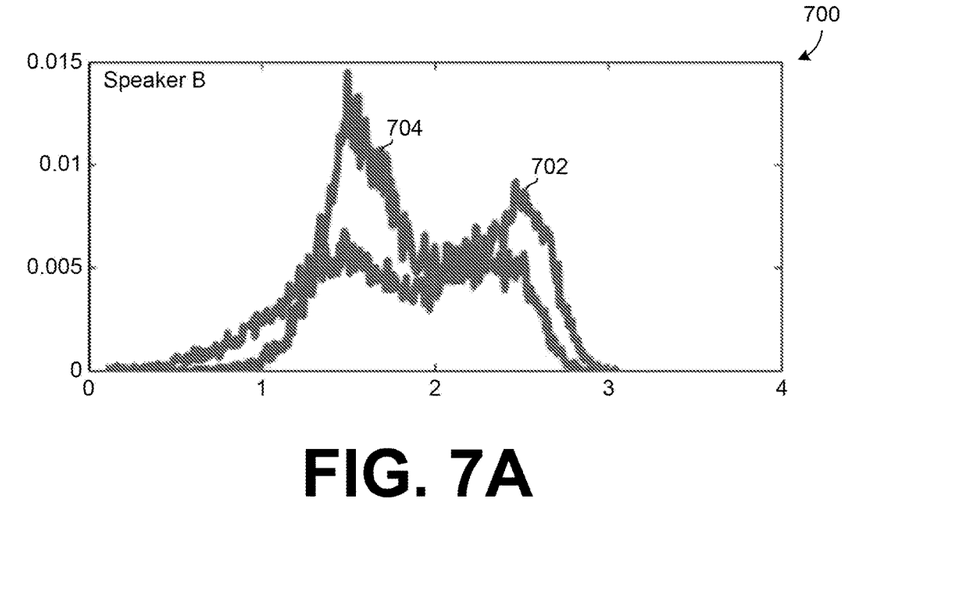
FIGS. 7A and 7B illustrate an example demonstrating how harmonicity distributions for two speakers may shift as they change from a stressed state to a more relaxed state.
Figure 7B:
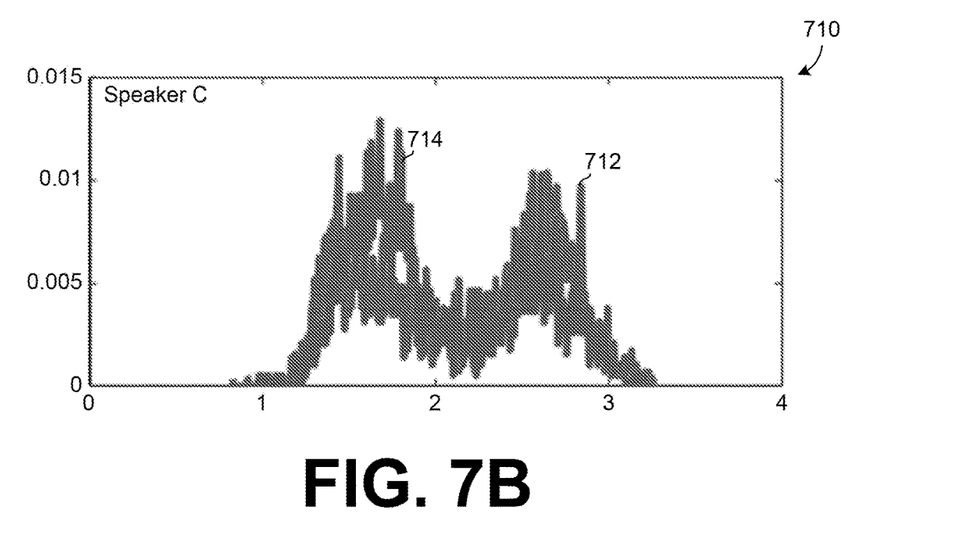

FIGS. 6-7 illustrate multiple examples of speech feature distributions for individual speakers or groups of speakers.

FIGS. 6A and 6B illustrate an example demonstrating how pitch distributions 600 and 610 for two speakers (Speaker A and Speaker B, respectively) shift when they change from a stressed state (e.g., at 602 and 612, respectively) to a more relaxed state (e.g., at 604 and 614, respectively) as a result of a therapy session, for example.

FIGS. 7A and 7B illustrate an example demonstrating how harmonicity distributions 700 and 710 for Speakers A and B, respectively, shift when they change from a stressed state (e.g., at 702 and 712, respectively) to a more relaxed state (e.g., at 704 and 714, respectively) as a result of a therapy session, for example.

Embodiments of the disclosed technology may be implemented as machine-directed methods or physical devices. Accordingly, certain implementations may take the form of an entirely-hardware embodiment, an entirely-software embodiment, or an embodiment combining both hardware and software aspects. For example, some or all of the components for any given embodiment may be computer-implemented components.

Figure 8:
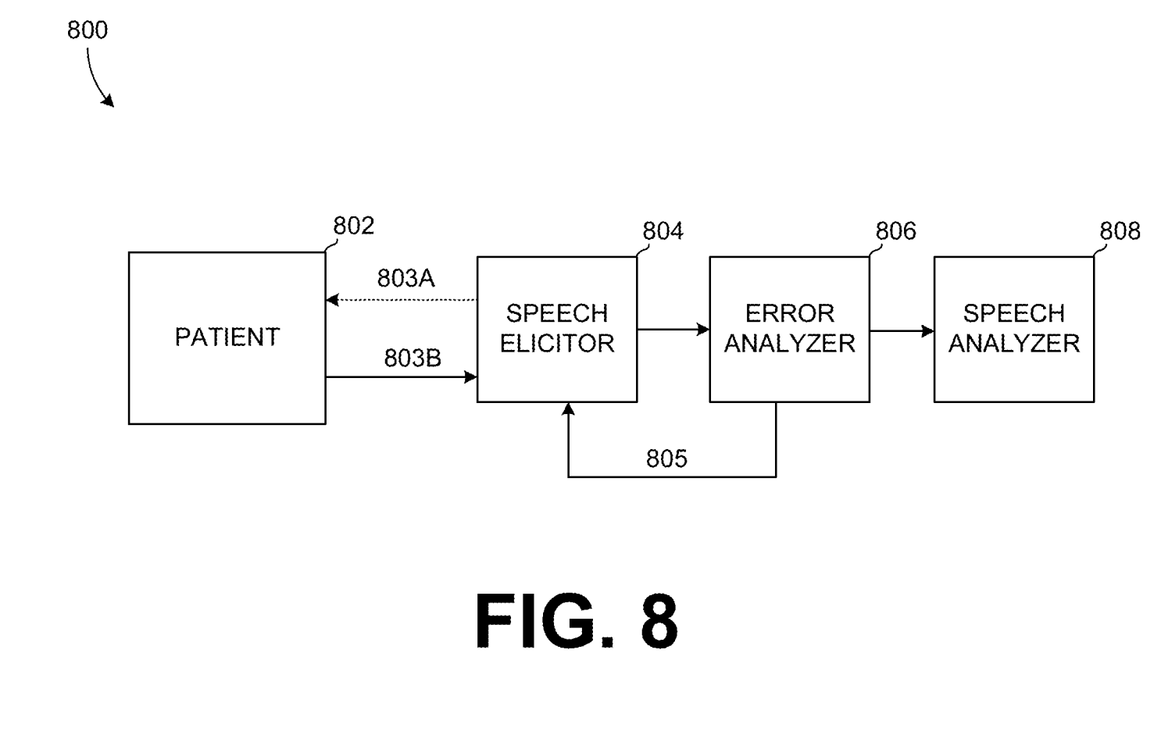
FIG. 8 is a block diagram illustrating an example of a speech collection system in accordance with certain embodiments of the disclosed technology.

FIG. 8 is a block diagram illustrating an example of a speech collection system 800 in accordance with certain embodiments of the disclosed technology. In the example, a speech elicitor 804 may prompt a speaker (e.g., a patient 802) to produce speech. For example, the speech elicitor 804 may present (e.g., visually, audibly, or both) any or all of the following questions 803A to the patient 802:

Tell me about your appetite today. What have you had to eat?
Tell me about your concentration today. Have you been able to focus? Have you been easily distracted?
Tell me about your sleep last night. When did you fall asleep? Did you have trouble sleeping? When did you wake up?
Please describe your day so far. What have you done? Where have you gone?
Please describe your energy level? How does your energy level impact your daily life?
Has anything made you smile today? Please tell me about it.
Generally speaking, where are you now? What is the environment like? Please describe your surroundings.
Have you been worried about anything lately? What?
Have you gotten exercise today? What did you do? How did you feel afterwards?
What are your plans for the next few days? Are there any events coming up? Any plans?

The speech produced (e.g., answers 803B provided by the patient 802) may then be provided as input to an error analyzer processing block 806. In certain embodiments, the data may be uploaded immediately if there is a suitable connection (e.g., a Wi-Fi connection) or, if no suitable connection is available at that time, the system may wait until a suitable connection is present before uploading a given session's responses.

The error analyzer 806 may analyze the speech and assess the quality of the speech. The error analyzer 806 may also scan for any errors. If errors are discovered or if the quality of speech is determined to not meet a particular threshold (e.g., if deemed sub-optimal or of poor quality), the error analyzer 806 may signal the speech elicitor 804 through a feedback communication mechanism 805, e.g., to once again prompt the speaker 802 to produce speech. This loop may continue until the speech quality meets the threshold (e.g., until good speech is produced), at which point the speech may be provided to a speech analyzer 808 such as those described elsewhere herein.

In certain implementations, the speech elicitor 804 may constantly record (and optionally store) speech in a circular buffer. In such embodiments, the error analyzer 806 may constantly analyze the data from the circular buffer. Whenever the speech quality threshold is met (e.g., when good speech is detected), that speech may then be provided as input to the speech analyzer 808 (which may proceed to process the good speech once it is received).

The speech elicitor 804 and the error analyzer 806 may be implemented within a single physical device, e.g., a mobile electronic device such as a smartphone. In certain implementations, speech elicitor 804, error analyzer 806, and some or all of the other components of the speech collection system 800 may function within a single physical device.

Certain implementations may include a method to provide as additional input to the speech analyzer metadata pertaining to the speaker (e.g., patient). Such metadata may include, for example, information about relevant events (e.g., being in a war). A speech analyzer algorithm may consider these inputs and thus produce a more accurate result. Additionally, these types of inputs may be used for testing and training purposes.

Speaker-related metadata may be provided as input in any of a number of various ways including, but not limited to, direct user input, input from the patient's doctor(s) and/or other care provider(s), and input from the patient's electronic medical records (EMRs).

In certain implementations, the collected speech data and/or speaker-related metadata may be uploaded to a relational database, which may be local or remotely hosted. The data may be stored on a per-subject and/or per-session basis, for example. It may be preferable for speakers to be identified only by an identification number (e.g., with no personally-identifiable information). Per-session data may include any or all of the following: the questions that were presented to the patient, the patient's responses (e.g., as audio files), the type of device that was used to record the speech, and timestamps associated with the questions, responses, and/or various user-interactions (e.g., button presses). The database may further provide information about which questions are deemed effective, which questions were skipped by the patient, and whether the patient paused before answering specific questions.

The following are examples of SQL statements that may be used to define a speech database such as that described above:

The following may be used to create a speech database:

```
CREATE DATABASE "ghcDB2"
    WITH OWNER postgres
    CONNECTION LIMIT -1;
```

The following may be used to create a question table within the speech database:

```
CREATE TABLE questionTable (
    questionID    varchar(64) NOT NULL PRIMARY KEY,
    content       varchar(1024) NOT NULL,
    enabled       boolean,
    audioFile     varchar(256)--bytea
);
```

The following may be used to create a user table within the speech database:

```
CREATE TABLE userTable (
    userID    varchar(256) NOT NULL PRIMARY KEY,
    pass      varchar(256) NOT NULL
--  gender    char(1) NOT NULL, --m/f
--  age       integer NOT NULL
);
```

The following may be used to create a session table within the speech database:

```
sessionID       uuid NOT NULL PRIMARY KEY,
userID          varchar(256) references userTable(userID),
sessionIssue    TIMESTAMP WITH TIME ZONE,
sessionSubmit   TIMESTAMP WITH TIME ZONE,
deviceType      varchar(256),
appVersion      varchar(256),
```

-continued

```
    serverVersion   varchar(256),
    submitted       boolean NOT NULL
);
```

The following may be used to create an answers table within the speech database:

```
CREATE TABLE answerTable (
    answerID        uuid NOT NULL PRIMARY KEY,
    sessionID       uuid references sessionTable(sessionID),
    questionID      varchar(64) references questionTable(questionID),
    questionNum     integer,
    -- status : (issued, answered, skipped, not_reached)
    status          varchar(64) NOT NULL,
    audioAnswerFile varchar(256)--BYTEA
);
```

The following may be used to create a meta events table within the speech database:

```
CREATE TABLE metaEventTable (
    eventID     uuid NOT NULL PRIMARY KEY,
    sessionID   uuid references sessionTable(sessionID),
    questionID  varchar(64) references questionTable(questionID),
    eventName   varchar(256) NOT NULL,
    eventTime   TIMESTAMP WITH TIME ZONE
);
```

Figure 9:
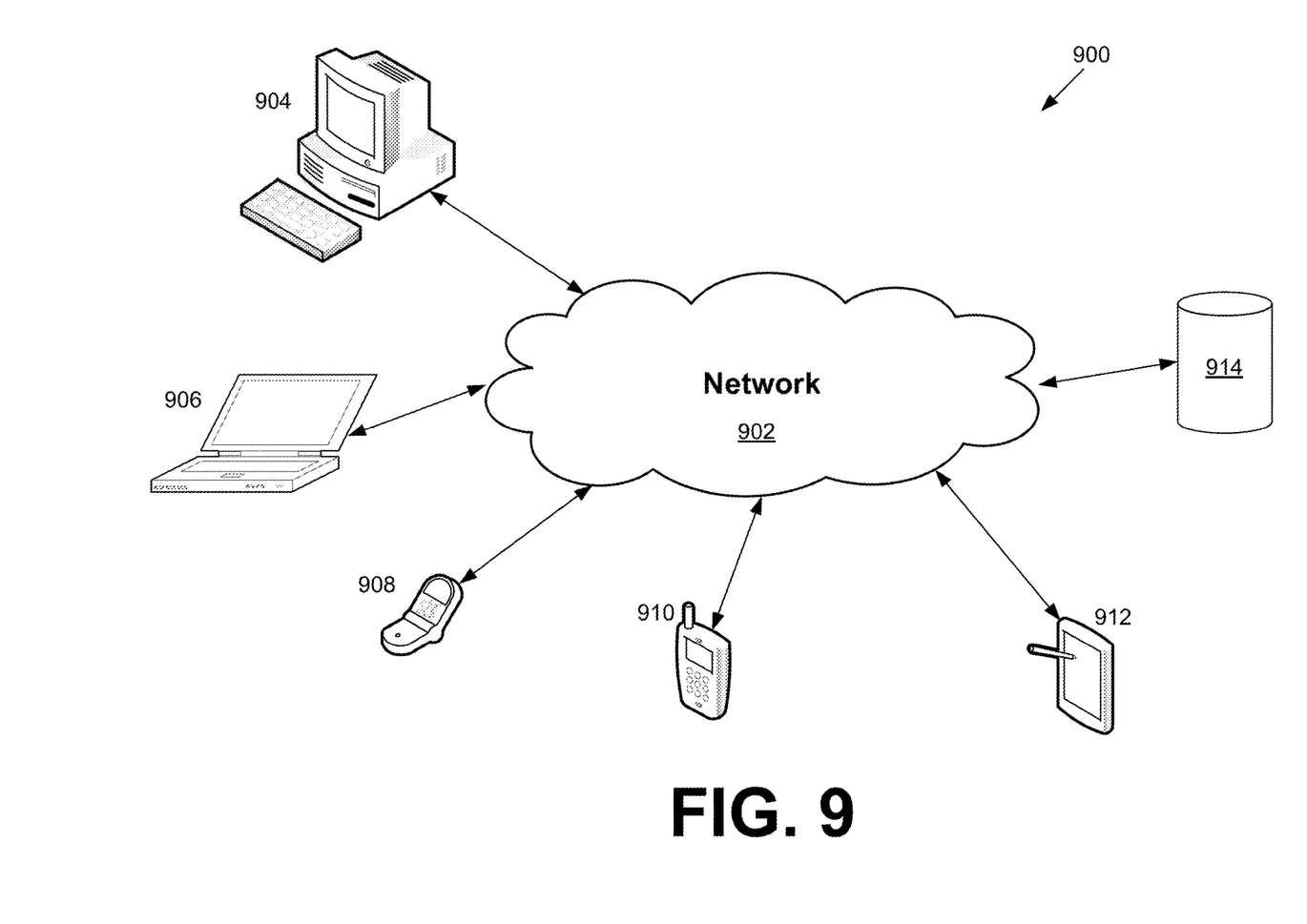
FIG. 9 is a block diagram illustrating an example of a networked system in which embodiments of the disclosed technology may be implemented.

FIG. 9 is a block diagram illustrating an example of a networked system 900 in which embodiments of the disclosed technology may be implemented. In the example, the system 900 includes a network 902 such as the Internet, an intranet, a home network, or any combination thereof. Traditional computing devices such as a desktop computer 904 and laptop computer 906 may connect to the network 902 to communicate with each other or with other devices connected to the network.

The networked system 900 also includes three mobile electronic devices 908-912. Two of the mobile electronic devices, 908 and 910, are mobile communications devices such as cellular telephones or smart phones. The third mobile electronic device, 912, is a handheld device such as a personal data assistant (PDA) or tablet device.

The networked system 900 also includes a storage device 914, which may be a central database or repository, a local data store, or a remote storage device, for example. The storage device 914 may be accessible to any or all of the other devices 904-912, subject to limitations or restrictions by the devices 904-912, a third party, or the storage device 914 itself. The storage device 914 may be used to store some or all of the public data that is accessed and/or used by any of the computers 904 and 906 or mobile electronic devices 908-912. In situations involving personal data, the storage device 914 may also store any or all of the personal data accessed and/or used by any of the computers 904 and 906 or mobile electronic devices 908-912.

Having described and illustrated the principles of the invention with reference to illustrated embodiments, it will be recognized that the illustrated embodiments may be modified in arrangement and detail without departing from such principles, and may be combined in any desired manner. And although the foregoing discussion has focused on particular embodiments, other configurations are contemplated. In particular, even though expressions such as "according to an embodiment of the invention" or the like are used herein, these phrases are meant to generally reference embodiment possibilities, and are not intended to limit the invention to particular embodiment configurations. As used herein, these terms may reference the same or different embodiments that are combinable into other embodiments.

Consequently, in view of the wide variety of permutations to the embodiments described herein, this detailed description and accompanying material is intended to be illustrative only, and should not be taken as limiting the scope of the invention. What is claimed as the invention, therefore, is all such modifications as may come within the scope and spirit of the following claims and equivalents thereto.

What is claimed is:

1. A computer-implemented method of improving output of a speech-based state-of-mind detection system, the method comprising:
   receiving, using the speech-based state-of-mind detection system, a speech pattern collected from a patient;
   determining, using the speech-based state-of-mind detection system, at least one feature of the collected speech pattern;
   determining, using the speech-based state-of-mind detection system, a presence or absence of a state-of-mind of the patient using a first distribution of a non-lexical speech feature computed over a first time interval in which speech of the patient is collected during a session and a second distribution of the non-lexical speech feature computed over a second time interval in which speech of the patient is collected during the session to indicate a change in the patient from a first state-of-mind to a second state-state-of-mind as a result of the session;
   wherein the state-of-mind is defined by a clinical protocol; and
   outputting, by the speech-based state-of-mind detection system, the presence or absence of the state-of-mind to the patient, a clinical expert, or both the patient and the clinical expert.

2. The computer-implemented method of claim 1, wherein the determined state-of-mind indicates a probability that the patient is suffering from at least one of:
   depression, suicidal tendencies, Post-Traumatic Stress Disorder (PTSD), a concussion, bipolar disorder, anxiety disorder, mild Traumatic Brain Injury (mTBI), and schizophrenia.

3. The computer-implemented method of claim 1, further comprising using at least the at least one non-lexical speech feature to build a predictor of the patient's state-of-mind.

4. The computer-implemented method of claim 3, wherein the using is performed on a remote server.

5. The computer-implemented method of claim 1, wherein the at least one non-lexical speech feature includes linguistic features and at least one of: prosodic features and spectral features.

6. The computer-implemented method of claim 1, wherein the at least one non-lexical speech feature corresponds to a pitch of the patient's speech.

7. The computer-implemented method of claim 1, wherein the at least one non-lexical speech feature corresponds to a harmonicity of the patient's speech.

8. The computer-implemented method of claim 1, further comprising comparing the determined state-of-mind to an empirical threshold.

9. The computer-implemented method of claim 1, further comprising: prompting the patient to produce the speech pattern; producing the speech pattern responsive to the prompting; and receiving the produced speech pattern.

10. The computer-implemented method of claim 9, further comprising analyzing the quality of the received speech pattern.

11. The computer-implemented method of claim 10, wherein analyzing the quality of the received speech pattern comprises determining whether the analyzed quality of the received speech pattern meets a particular threshold.

12. The computer-implemented method of claim 11, further comprising causing the prompting, producing, receiving, and analyzing to repeat until the analyzed quality of the received speech pattern meets the particular threshold.

13. The computer-implemented method of claim 9, wherein prompting the patient to produce the speech pattern comprises presenting to the patient a plurality of open-ended questions.

14. A system for improving output of an automated speech-based state-of-mind detection process, the system comprising at least one processor configured to:
receive, using the speech-based state-of-mind detection process, a speech pattern collected from a patient;
compute, from the collected speech pattern, using the speech-based state-of-mind detection process, at least one non-lexical speech feature that indicates a condition of equipment used to collect the speech pattern or a physical environment in which the speech pattern was collected;
determine a presence or absence of a state-of-mind of the patient using the at least one computed non-lexical speech feature that indicates a condition of equipment used to collect the speech pattern or a physical environment in which the speech pattern was collected,
wherein the state-of-mind is defined by a clinical protocol,
wherein the presence or absence of the state-of-mind is using at least one model that models speech patterns of healthy speakers and models speech patterns of speakers that have been positively diagnosed with the state-of-mind; and
outputting, by the speech-based state-of-mind detection process, an indication of the presence or absence of the state-of-mind to the patient, a clinical expert, or both the patient and the clinical expert.

15. The system of claim 14, wherein the at least one processor is configured to:
store speech assessment information; and
develop an algorithm configured to be used by the mental health determination module in determining the state-of-mind of the patient.

16. The system of claim 14, wherein the at least one processor is configured to interact with the mental health determination module over a network.

17. The system of claim 16, wherein the network is the Internet.

18. The system of claim 14, wherein the at least one processor is configured to use at least the at least one computed speech feature to build a predictor of the patient's state-of-mind.

19. The system of claim 14, wherein the at least one processor is a same processor.

20. The system of claim 14, wherein the determined state-of-mind indicates a probability that the patient is suffering from at least one of: depression, suicidal tendencies, Post-Traumatic Stress Disorder (PTSD), a concussion, bipolar disorder, anxiety disorder, mild Traumatic Brain Injury (mTBI), and schizophrenia.

21. The system of claim 14, wherein the at least one computed speech feature includes linguistic features and at least one of: prosodic features and spectral features.

22. The system of claim 14, wherein the at least one speech feature corresponds to a pitch of the patient's speech.

23. The system of claim 14, wherein the at least one speech feature corresponds to a harmonicity of the patient's speech.

24. The system of claim 14, wherein the collected speech pattern comprises an answer to a question that was presented to the patient.

25. The system of claim 14, wherein the collected speech pattern comprises a plurality of answers, each answer corresponding to one of a plurality of questions that were presented to the patient.

26. The system of claim 14, wherein the at least one processor is configured to check the audio quality of the collected speech pattern.

27. A computer-implemented method for improving output of a speech-based state-of-mind detection system, the method comprising:
receiving, by the speech-based state-of-mind detection system, a speech pattern collected from a patient;
computing, by the speech-based state-of-mind detection system, a plurality of speech features from the collected speech pattern;
determining, by the speech-based state-of-mind detection system using the plurality of speech features, a presence or absence of a state-of-mind of the patient;
wherein the state-of-mind is defined by a clinical protocol,
wherein the presence or absence of the state-of-mind is determined using at least one model that models speech patterns of healthy speakers and models speech patterns of speakers that have been positively diagnosed with the state-of-mind,
wherein the plurality of speech features comprises at least two of any of the following: Damped Oscillator Cepstral Coefficients (DOCCs), Normalized Modulation Cepstral Coefficients (NMCCs), Medium Duration Speech Amplitudes (MMeDuSA), Gammatone Cepstral Coefficients (GCCs), DeepTVs, a syllable duration, a speaking rate, a speech rhythmicity, a tilt feature;
outputting, by the speech-based state-of-mind detection system, the determined state-of-mind to the patient or a clinical expert or both the patient and the clinical expert.

* * * * *